United States Patent
Zheng et al.

(10) Patent No.: US 11,253,730 B2
(45) Date of Patent: Feb. 22, 2022

(54) ULTRASOUND DEEP BRAIN STIMULATION METHOD AND SYSTEM

(71) Applicant: GreenValley BrainTech (Shenzhen) Medical Technology Co., Ltd., Shenzhen (CN)

(72) Inventors: Hairong Zheng, Guangdong (CN); Lili Niu, Guangdong (CN); Congzhi Wang, Guangdong (CN); Ming Qian, Guangdong (CN); Yang Xiao, Guangdong (CN); Long Meng, Guangdong (CN)

(73) Assignee: GREENVALLEY BRAINTECH (SHENZHEN) MEDICAL TECHNOLOGY CO., LTD., Shenzhen (CN)

( * ) Notice: Subject to any disclaimer, the term of this patent is extended or adjusted under 35 U.S.C. 154(b) by 607 days.

(21) Appl. No.: 15/630,623

(22) Filed: Jun. 22, 2017

(65) Prior Publication Data

US 2017/0291044 A1 Oct. 12, 2017

Related U.S. Application Data

(63) Continuation of application No. PCT/CN2015/078373, filed on May 6, 2015.

(30) Foreign Application Priority Data

Dec. 26, 2014 (CN) .......................... 201410829230.9

(51) Int. Cl.
*A61N 7/02* (2006.01)
*A61B 5/00* (2006.01)
(Continued)

(52) U.S. Cl.
CPC .............. *A61N 7/02* (2013.01); *A61B 5/0036* (2018.08); *A61B 5/0042* (2013.01); *A61B 5/055* (2013.01);
(Continued)

(58) Field of Classification Search
CPC ...... A61B 2562/0209; A61B 2562/046; A61B 5/0042; A61B 5/04001; A61B 5/0484;
(Continued)

(56) References Cited

U.S. PATENT DOCUMENTS 5,038,787 A * 8/1991 Antich ................. A61B 8/0875
600/437
6,609,030 B1 8/2003 Rezai et al.
(Continued)

FOREIGN PATENT DOCUMENTS

| CN | 101663013 | 3/2010 |
| CN | 102149428 | 8/2011 |

(Continued)

OTHER PUBLICATIONS

Bæk et al (Modeling transducer impulse responses for predicting calibrated pressure pulses with the ultrasound simulation program Field II, The Journal of the Acoustical Society of America 127, 2825 (2010) (Year: 2010).*

(Continued)

*Primary Examiner* — Joanne M Hoffman
*Assistant Examiner* — Alexei Bykhovski
(74) *Attorney, Agent, or Firm* — Hamre, Schumann, Mueller & Larson, P.C.

(57) ABSTRACT

An ultrasound deep brain stimulation method and system, the ultrasound deep brain stimulation method comprises: medically imaging a head of an animal or a human being, to generate image data; creating a head 3D digital model according to the image data; creating a 3D digital model of
(Continued)

an ultrasound transducer array according to structure, density and acoustic parameters information of the ultrasound transducer array; generating a first ultrasound transmitting sequence according to the head 3D digital model, the 3D digital model of the ultrasound transducer array, structure, density and acoustic parameters of the skull and brain tissues, and structure, density and acoustic parameters of the ultrasound transducer array; and controlling the ultrasound transducer array to transmit ultrasound waves in accordance with the first ultrasound transmitting sequence, to implement ultrasound deep brain stimulation to the brain nucleus to be stimulated. By the use of the present invention, ultrasound can noninvasively passes through the skull to be focused in a deep brain region. By the use of different ultrasound transmitting sequences, ultrasound neuromodulation can be realized, and research on an action mechanism for the ultrasound neuromodulation can be performed.

17 Claims, 8 Drawing Sheets

(51) Int. Cl.
| | | |
|---|---|---|
| *A61B 5/055* | | (2006.01) |
| *G16H 50/50* | | (2018.01) |
| *A61B 5/24* | | (2021.01) |
| *A61B 5/377* | | (2021.01) |
| *G16Z 99/00* | | (2019.01) |
| *A61N 7/00* | | (2006.01) |

(52) U.S. Cl.
CPC ............... *A61B 5/24* (2021.01); *A61B 5/377* (2021.01); *A61B 5/7239* (2013.01); *G16H 50/50* (2018.01); *G16Z 99/00* (2019.02); *A61B 2562/0209* (2013.01); *A61B 2562/046* (2013.01); *A61N 2007/0026* (2013.01); *A61N 2007/0052* (2013.01); *A61N 2007/0073* (2013.01); *A61N 2007/0082* (2013.01)

(58) Field of Classification Search
CPC ..... A61B 5/055; A61B 5/4836; A61B 5/7239; A61N 2007/0026; A61N 2007/0052; A61N 2007/0073; A61N 2007/0082; A61N 7/02; G06F 19/00; G16H 50/50
See application file for complete search history.

(56) References Cited

U.S. PATENT DOCUMENTS

| | | | |
|---|---|---|---|
| 6,827,681 | B2 | 12/2004 | Tanner et al. |
| 2005/0277824 | A1* | 12/2005 | Aubry ..................... A61B 8/00 600/407 |
| 2007/0016042 | A1* | 1/2007 | Kawabata ................ A61B 8/08 600/439 |
| 2010/0202001 | A1* | 8/2010 | Miller .................... A61B 6/583 358/1.9 |
| 2011/0092800 | A1 | 4/2011 | Yoo et al. |
| 2012/0283604 | A1 | 11/2012 | Mishelevich |
| 2013/0131495 | A1* | 5/2013 | Konofagou .......... A61B 8/0808 600/411 |
| 2013/0197401 | A1 | 8/2013 | Sato et al. |
| 2014/0142664 | A1 | 5/2014 | Roukes et al. |
| 2015/0151142 | A1* | 6/2015 | Tyler ........................ A61B 8/06 601/2 |
| 2015/0297176 | A1* | 10/2015 | Rincker ................. A61B 8/429 600/439 |

FOREIGN PATENT DOCUMENTS

| | | |
|---|---|---|
| CN | 102283145 | 12/2011 |
| CN | 102462892 | 5/2012 |
| CN | 102470247 | 5/2012 |
| CN | 102762253 | 10/2012 |
| CN | 202538169 | 11/2012 |
| CN | 103028202 | 4/2013 |
| CN | 103432691 | 12/2013 |
| CN | 104548390 | 4/2015 |

OTHER PUBLICATIONS

Halpern et al., "Deep Brain Stimulation for Epilepsy", Neurotherapeutics: The Journal of the American Society for Experimental NeuroTherapeutics, vol. 5, Jan. 2008, pp. 59-67.
Kirton et al., "Contralesional repetitive transcranial magnetic stimulation for chronic hemiparesis in subcortical paediatric stroke: a randomised trial", Lancet Neurol, vol. 7, Jun. 2008, pp. 507-513.
Tyler et al., "Remote Excitation of Neuronal Circuits Using Low-Intensity, Low-Frequency Ultrasound", PLoS ONE, vol. 3, issue 10, Oct. 2008, 11 pages; available at http://journals.plos.org/plosone/article?id=10.1371/journal.pone.0003511.
Tufail et al., "Transcranial Pulsed Ultrasound Stimulates Intact Brain Circuits", Neuron, vol. 66, Jun. 10, 2010, pp. 681-694.
Legon et al., "Transcranial focused ultrasound modulates the activity of primary somatosensory cortex in humans", Nature Neuroscience, vol. 17, No. 2, Feb. 2014, pp. 322-329.
Office Action and Search Report, issued in the corresponding Chinese patent application No. 201410829230.9, dated Feb. 15, 2017, 11 pages.
International Search Report, issued in the corresponding PCT/CN2015/078373, dated Sep. 10, 2015, 8 pages.

* cited by examiner

ULTRASOUND DEEP BRAIN STIMULATION METHOD AND SYSTEM

FIELD OF THE INVENTION

The invention relates to an ultrasound brain stimulation technology, and in particular to an ultrasound deep brain stimulation method and system.

BACKGROUND OF THE INVENTION

Under the influence of factors such as social aging and deepening mental stress and the like, the number of patients of neurologic and psychiatric diseases including Parkinson's disease, muscle tension disorder, obsessive-compulsive disorder, depressive disorder, epilepsy and the like has increased dramatically all over the world, and currently the patients around the world have been more than 560,000,000. German scientists report that cerebral cortex of a dog under electric stimulation may result in a particular body reaction. Such important finding had given rise to series of intervention technologies such as transcranial electrical stimulation, transcranial magnetic stimulation, nerve implantation and the like in the century from then on, which greatly promotes people's understanding of functional localization of cerebral cortex and research and development of brain disease research instruments, and opens a new chapter for brain function regulation such as emotion, memory, cognition and the like and for psychological and mental disease intervention treatment.

A nervous system is a system that plays a leading role in an organism. A central nervous system mediates generation of advanced functions such as emotion, attention, learning, memory and the like, participates in generation of feelings and initiation of voluntary motion. A neuron is a functional unit of the nervous system that plays a variety of functions. Neurons form a mesh through synapses to contact with each other and transfer information, and form a sensory system, a motor system and the like, and each system can be divided into several sub systems, such as visual sense, sense of smell, sense of hearing, taste sense, body surface tactile sense, or the like, and implementation of the functions relies on a neural circuit formed by accurate association of different types of cells that are at different positions of the nervous system. The neural circuit is a bridge which associates molecular and cellular functions with the overall behavior function. Research on a particular functional neural circuit is helpful to understand formation and modification of the neural circuit, information coding, processing and handling, and relationship between the neural circuit and a behavior, so as to understand the working principle of the brain at a deeper level.

Neuromodulation is an effective means of conducting research on neural circuits, and Deep Brain Stimulation (DBS), also called "brain pacemaker", is a new therapy in which a surgical department of nervous system diseases is combined with a technology of electronics, a stereotactic operation is adopted to implant micro electrodes into targets in the brain of a patient, to suppress abnormal functions of target cells through controllable electrical stimulation, so as to achieve the purpose of effectively intervene diseases (see the Chinese patent CN 102470247 A, CN 102762253 A4). This technology is currently the only technical means by which a direct contact with the deep brain can be established and brain activity can be intervened and thus brain diseases can be treated. Since this technology was used in control of tremor for the first time in 1987, there are more than 100,000 patients all over the world into whose brains DBS devices are implanted, which provides an effective new intervention method for many intractable brain diseases such as depressive disorder, Parkinson's disease, intractable epilepsy, muscle tension imbalance, intractable pain and the like [Halpem C H, Samadani U, Litt B, et al. Deep brain stimulation for epilepsy. Neurotherapeutics, 2008, 5(1): 59-67.]

Technologies such as transcranial direct current stimulation (tDCS) and transcranial magnetic stimulation (TMS) and the like are painless and noninvasive detection and treatment technologies. By means of tDCS, a constant current is inputted to a particular region within the cranium via two scalp-attached electrode slices that are soaked by salt water, to change a depolarized or hyperpolarized direction of a membrane potential of neurons on the surface of the brain, so as to change cortical excitability of a spontaneous neural activity [CN 202538169 U]. The TMS generates a magnetic field domain vertical to a plane of a coil by an instantaneous and high-voltage pulse produced by a magnetic coil placed on the scalp, the magnetic field domain passes through the scalp and skull almost without attenuation to reach deep tissues of the brain and generate an induction current, to depolarize nerve cells and generate an evoked potential. Exciting or suppressive characteristics of the nerve cell is controlled in such a mode as single pulse, double pulse and repetitive transcranial magnetic stimulation and the like, so as to regulate functions of a cortical layer (see the Chinese patent CN 102462892 A and the U.S. Pat. No. 6,827,681 B2 and Kirton A, Chen R, Friefeld S, Gunraj C, Pontigon A-M, et al. (2008) Contralesional repetitive transcranial magnetic stimulation for chronic hemiparesis in subcortical paediatric stroke: a randomised trial. The Lancet Neurology 7: 507-513.). Both of the technologies are used for evaluating nerve electrophysiological conduction path and for neurological rehabilitation treatment of diseases such as depressive disorder, epilepsy, stroke, schizophrenia, autism and the like.

A Drug Delivery Pump technology realizes neuromodulation by means of direct delivery of drug by implanting a pump device at an accurate position (see the U.S. Pat. No. 6,609,030 B1). Due to the drug's direct effect to a local part, drug dosage is effectively reduced and thus side effect is reduced. It has become a basic method to treat spasm originates from intractable spinal cord or brain by long-term intrathecal use of baclofen by implanted pumps. Optogenetics is a powerful means for exploring the nerve circuit (see the Chinese patent CN 102283145 A and the US patent US 20140142664 A1). The basic principle of Optogenetics is that opsin gene combined with a specific promoter is imported into a particular group of neurons through virus transfection, and physiological activities of the neurons are changed by photostimulation with different parameters, so as to realize regulation of a neural pathway to which the neurons belong.

Transcranial ultrasound neuromodulation is a new technology of noninvasive brain stimulation that has appeared in recent years, by which nervous centralis of the stimulated site produces a stimulating or inhibiting effect through different intensities, frequencies, pulse repetition frequencies, pulse widths and durations, so as to produce a two-way regulating reversible change to the neurologic function (see the US patent US20130197401, US20110092800). Recently an experimental group from Arizona State University has proved through a mouse brain hippocampal slice experiment that low-frequency low-voltage ultrasound induces neuromodulation, and the group has also proposed a possible regulation mechanism, i.e., ultrasound affects voltage-gated sodium and calcium channels [Tyler W J, Tufail Y, Finsterwald M, Tauchmann M L, Olson E J, et al. (2008) Remote excitation of neuronal circuits using low-intensity, low-frequency ultrasound. PLoS One 3: e3511.]. Later, the group proved for the first time through a living animal experiment that low-frequency low-voltage ultrasound realizes neuromodulation [Tufail Y, Matyushov A, Baldwin N, Tauchmann M L, Georges J, et al. (2010) Transcranial pulsed ultrasound stimulates intact brain circuits. Neuron 66: 681-694.]. Legon Wynn and etc. from Carilion research institution of Virginia Tech University apply low-frequency low-voltage ultrasound directly to a particular region of the brain, which can strengthen people's discernibility on tactile sense. This discovery proved for the first time that low-intensity transcranial focused ultrasound can regulate human brain activities and improve perception ability [Legon W, Sato T F, Opitz A, Mueller J, Barbour A, et al. (2014) Transcranial focused ultrasound modulates the activity of primary somatosensory cortex in humans. Nature neuroscience 17: 322-329.].

Although clinical or scientific experiment effect of the above-described brain stimulation and neuromodulation technologies has been affirmed, mechanism of action of which has not been clear yet. It is currently regarded that brain stimulation changes activity of voltage-gated channels, neurotransmitters are exhausted, such that transmission of synaptic information is hindered and output of neural signals around the electrodes is inhibited, which produces a functional damage effect on the stimulated nuclei; the stimulation functions on axon terminals that are in synaptic connections with the neurons around the electrodes, which regulates the output of the neural signals indirectly and thus changes pathological neural network function.

The above-described various brain stimulation devices still have limitations and technology challenges in many aspects. For example, the DBS is an invasive technology, the device is experience and the operation cost is high, there are certain risks such as surgery complications, targets tolerance, rejection reaction and the like, the power battery has a service life of 4-5 years, so that reoperation is necessary to replace the battery or an internal stimulator after the battery runs out, which causes more pain and economic burden to the user and thus limits popularization of the DBS to a great extent. The noninvasive tDCS and TMS technologies have high requirements on the operator and experimental conditions, and results thereof are affected by factors such as treatment frequency, stimulation site, duration of the stimulation, disease severity, drug treatment and the like, so that evaluation of therapeutic efficiency is debatable. Optogenetics has limitations, such as use of a wide field stimulation mode, which can activate or suppress neurons, but it may activate the whole animal sample or the whole neural circuit, thus it is impossible to realize selective photostimulation activation of particular cells or a group of cells; if a technology is adopted based on a scan mirror, an acoustooptical deflector, a light emitting diode matrix, a spatial light modulator, a liquid crystal or a micro reflector, although the cells can be activated by stimulation at a high spatial and temporal resolution, generally the cells must be combined on an inversely or forwardly installed fluorescence microscope, which is only suitable for photostimulation activation of cultured cells and brain slices, and has limitations in small photostimulation scope, being not suitable for research on large nervous network and regulation of behavior activities of living animals. These facts limit the application of the Optogenetics technology in research of neural circuit. Furthermore, incompatibility of the above-described devices with MRI has not been properly solved.

Transcranial ultrasound neuromodulation technology realizes cranial neuromodulation function by use of low-frequency low-intensity ultrasound, but the existing ultrasound modulation devices are simple due to single point regulation, and currently mechanism of ultrasound neuromodulation is not clear.

SUMMARY OF THE INVENTION

The invention provides an ultrasound deep brain stimulation method and system, which noninvasively passes through a skull to enter a deep brain region, to obtain an optimum ultrasound transmitting sequence required for transmitting transcranial focused ultrasound.

In order to achieve the above purpose, the present invention provides an ultrasound deep brain stimulation method, comprising:

medically imaging a head of an animal or a human being, to generate image data;

creating a head 3D digital model according to the image data;

creating a 3D digital model of an ultrasound transducer array according to structure, density and acoustic parameters information of the ultrasound transducer array;

generating a first ultrasound transmitting sequence according to the head 3D digital model, the 3D digital model of the ultrasound transducer array, structure, density and acoustic parameters of the skull and brain tissues, and structure, density and acoustic parameters of the ultrasound transducer array;

controlling the ultrasound transducer array to transmit ultrasound waves in accordance with the first ultrasound transmitting sequence, to implement ultrasound deep brain stimulation to the brain nucleus to be stimulated.

In one embodiment, the ultrasound deep brain stimulation method further comprises: selecting position(s) of one or more brain nucleus to be stimulated, and locating the position of the brain nucleus to be stimulated at the head 3D digital model.

In one embodiment, generating a first ultrasound transmitting sequence according to the head 3D digital model, the 3D digital model of the ultrasound transducer array, structure, density and acoustic parameters of the skull and brain tissues, and structure, density and acoustic parameters of the ultrasound transducer array, comprises:

placing virtual sound sources at one or more positions that need to be focused, and simulating propagating behavior of ultrasound wave emitted from the virtual sound sources in the head 3D digital model;

simulating a voltage signal of the ultrasound transducer array when the ultrasound wave is propagated to a virtual spatial position where the ultrasound transducer array is located;

performing time reversal to the voltage signal to generate a first time reversal signal as the first ultrasound transmitting sequence.

In one embodiment, simulating a voltage signal of the ultrasound transducer array when the ultrasound wave is propagated to a virtual spatial position where the ultrasound transducer array is located, comprises:

simulating a sound intensity signal and a sound pressure signal of the ultrasound wave on ultrasound transducer array surface, and simulating a voltage signal of the ultrasound transducer array according to the sound intensity signal and the sound pressure signal and piezoelectric conversion parameters of the ultrasound transducer array.

In one embodiment, the ultrasound deep brain stimulation method further comprises: adjusting virtual spatial positions of the head 3D digital model and the 3D digital model of the ultrasound transducer array according to actual spatial positions.

In one embodiment, the ultrasound deep brain stimulation method further comprises: calculating acoustic parameters of the head according to the structure and density of the skull and brain tissues.

In one embodiment, the ultrasound deep brain stimulation method further comprises:

placing the virtual sound source in a focus region which does not need stimulation, to obtain a second time reversal signal;

performing phase reverse to the second time reversal signal to generate a reverse signal;

combining the reverse signal with the first time reversal signal, as a second ultrasound transmitting sequence;

controlling the ultrasound transducer array to transmit ultrasound waves in accordance with the second ultrasound transmitting sequence, to implement ultrasound deep brain stimulation to the brain nucleus to be stimulated.

In one embodiment, the ultrasound deep brain stimulation method further comprises: acquiring sound field focus position and shape after the ultrasound passes through the skull by using an imaging sequence of a magnetic resonance imaging system, and adjusting the first ultrasound transmitting sequence or the second ultrasound transmitting sequence according to the sound field focus position and shape and the head 3D digital model to change position and shape of an ultrasound focusing point.

In one embodiment, an ultrasound deep brain stimulation result is acquired using a functional magnetic resonance imaging technology, and a fine tuning is performed to an ultrasound focusing position according to the ultrasound deep brain stimulation result.

In one embodiment, the medically imaging a head of an animal or a human being, to generate image data, comprises: performing a 3D magnetic resonance imaging scan and a 3D CT imaging scan to the head of an animal or a human being, to generate image data.

In one embodiment, creating a head 3D digital model according to the image data, comprises: performing 3D reconstruction and registration of the image data, to create the head 3D digital model of the animal or the human being that includes structure, density and acoustic parameters of the skull and brain tissues.

In one embodiment, placing virtual sound sources at one or more positions that need to be focused, and simulating propagating behavior of ultrasound wave emitted from the virtual sound sources in the head 3D digital model, comprises: placing virtual sound sources at one or more positions that need to be focused, and simulating propagating behavior of ultrasound wave emitted from the virtual sound sources in the head 3D digital model by using a linear wave equation, a nonlinear wave equation, a finite time difference method or a k space virtual spectrum method.

In one embodiment, the shape of the ultrasound transducer array comprises: a flat plate, a sphere and an arc surface, and meanwhile the ultrasound transducer array is compatible with the magnetic resonance imaging system.

In one embodiment, the imaging sequence is an imaging sequence in which tissue displacement produced by an acoustic field is observed, or an imaging sequence in which temperature change produced by the ultrasonic sound field is observed.

In one embodiment, modes for implementing ultrasound deep brain stimulation to the brain nucleus to be stimulated include: a pulse mode, a multiple period mode and an encoding mode.

In order to achieve the above purpose, the present invention provides an ultrasound deep brain stimulation method, comprising:

medically imaging a head of an animal or a human being, to generate image data;

creating a head 3D digital model according to the image data;

inputting the head 3D digital model to a 3D printer to generate an ultrasound transmitting sequence;

controlling the ultrasound transducer array to transmit ultrasound waves in accordance with the ultrasound transmitting sequence, to implement ultrasound deep brain stimulation to the brain nucleus to be stimulated.

In one embodiment, the ultrasound deep brain stimulation method further comprises: selecting position(s) of one or more brain nucleus to be stimulated, and locating the position of the brain nucleus to be stimulated at the head 3D digital model.

In one embodiment, inputting the head 3D digital model to a 3D printer to generate an ultrasound transmitting sequence, comprises:

inputting the head 3D digital model to a 3D printer to obtain a model of the skull;

putting the ultrasound transducer array and the model of the skull in a water tank;

the ultrasound transducer array receives ultrasound wave emitted from a sound source placed at a position that needs to be focused, and generating a voltage signal according to the ultrasound wave;

performing time reversal to the voltage signal to generate a time reversal signal as the ultrasound transmitting sequence.

In one embodiment, an ultrasound deep brain stimulation result is acquired using a functional magnetic resonance imaging technology, and a fine tuning is performed to an ultrasound focusing position according to the ultrasound deep brain stimulation result.

In one embodiment, the ultrasound deep brain stimulation method further comprises: acquiring sound field focus position and shape after the ultrasound passes through the skull by using an imaging sequence of a magnetic resonance imaging system, and adjusting the ultrasound transmitting sequence according to the sound field focus position and shape and the head 3D digital model to change position and shape of an ultrasound focusing point.

In one embodiment, an ultrasound deep brain stimulation result is acquired using a functional magnetic resonance imaging technology, and a fine tuning is performed to an ultrasound focusing position according to the ultrasound deep brain stimulation result.

In one embodiment, the medically imaging a head of an animal or a human being, to generate image data, comprises: performing a 3D magnetic resonance imaging scan and a 3D CT imaging scan to the head of an animal or a human being, to generate image data.

In one embodiment, creating a head 3D digital model according to the image data, comprises: performing 3D reconstruction and registration of the image data, to create the head 3D digital model of the animal or the human being that includes structure, density and acoustic parameters of the skull and brain tissues.

In one embodiment, the shape of the ultrasound transducer array comprises: a flat plate, a sphere and an arc surface, and meanwhile the ultrasound transducer array is compatible with the magnetic resonance imaging system.

In one embodiment, modes for implementing ultrasound deep brain stimulation to the brain nucleus to be stimulated include: a pulse mode, a multiple period mode and an encoding mode.

In order to achieve the above purpose, the present invention provides an ultrasound deep brain stimulation system, comprising: a medical imaging equipment, an MRI system, an ultrasound transmitting/receiving control system, a host control computer, an MRI control system and a power supply management system; the host control computer is connected to the medical imaging equipment, the ultrasound transmitting/receiving control system and the MRI control system; the MRI system is connected to the MRI control system; the MRI system is provided therein with an ultrasound transducer array, a head fixing and locating device, wherein the head fixing and locating device is used for fixing the head, the ultrasound transducer array is disposed around the head fixing and locating device and is connected to the ultrasound transmitting/receiving control system;

the medical imaging equipment is used for photographing a head image, and reconstructing a head 3D digital model according to the head image;

the host control computer creates a 3D digital model of the ultrasound transducer array according to structure, density and acoustic parameter information of the ultrasound transducer array, and generates an ultrasound transmitting sequence according to the head 3D digital model and the 3D digital model of the ultrasound transducer array, and then sends an ultrasound deep brain stimulation instruction to the ultrasound transmitting/receiving control system;

the ultrasound transmitting/receiving control system receives the ultrasound deep brain stimulation instruction, controls the ultrasound transducer array according to the ultrasound deep brain stimulation instruction to transmit ultrasound wave to the brain nucleus to be stimulated in accordance with the ultrasound transmitting sequence to implement ultrasound deep brain stimulation;

the MRI control system controls the MRI system to monitor actual position and shape of an ultrasound focusing point in real time, to adjust the ultrasound transmitting sequence according to frequency, pulse duration, pulse length, pulse repetition frequency and intensity.

In one embodiment, the ultrasound deep brain stimulation system further comprises: a 3D printer, a water tank and a sound source;

the 3D printer is used for printing a skull model according to the head 3D digital model;

the water tank is used for housing the skull model and the ultrasound transducer array;

the sound source is placed at a position to be focused, for sending out ultrasound wave to the ultrasound transducer array placed in the water tank.

In one embodiment, the shape of the ultrasound transducer array includes: a flat plate, a sphere and an arc surface.

The ultrasound deep brain stimulation system and method provide a high spatial resolution (1~2 mm), and the system can noninvasively passes through the skull to enter a deep brain region. An optimum ultrasound transmitting sequence required for transmitting transcranial focused ultrasound by an ultrasound time reversal method, and actual position and shape of the ultrasound focusing point can be monitored in real time by the magnetic resonance imaging system, to adjust the transmitting sequence depending on time (frequency, pulse duration, pulse length, pulse repetition frequency, intensity, and etc.), so as to realize targeted region regulation. The spatial resolution of a given electromagnet TMS is fixed. For eDCS, only position of the electrode, type, current amplitude and stimulation duration can be changed. In addition, by use of different ultrasound transmitting sequences, research on ultrasound neuromodulation mechanism (an acoustic radiation force, acoustic streaming, shock wave, cavitation effect and etc.) can be performed.

BRIEF DESCRIPTION OF THE DRAWINGS

In order to describe the embodiment of the invention or technical solutions in prior art more clearly, hereinafter accompanying figures required to be used in description of the embodiment or the prior art will be introduced briefly. Obviously, the accompanying figures in the following description are merely some embodiments of the invention, and it is practicable for those skilled in the art to obtain other accompanying figures according to these ones in the premise of making no creative efforts.

DETAILED DESCRIPTION OF THE PREFERRED EMBODIMENTS

Hereinafter the technical solution in the embodiments of the present invention will be described clearly and integrally in combination with the accompanying drawings in the embodiments of the present invention, and obviously the described embodiments are merely part of the embodiments, not all of the embodiments. On the basis of the embodiment in the invention, all of the other embodiments obtained by those skilled in the art in the premise that no creative efforts are made fall within the protection scope of the invention.

Figure 1:
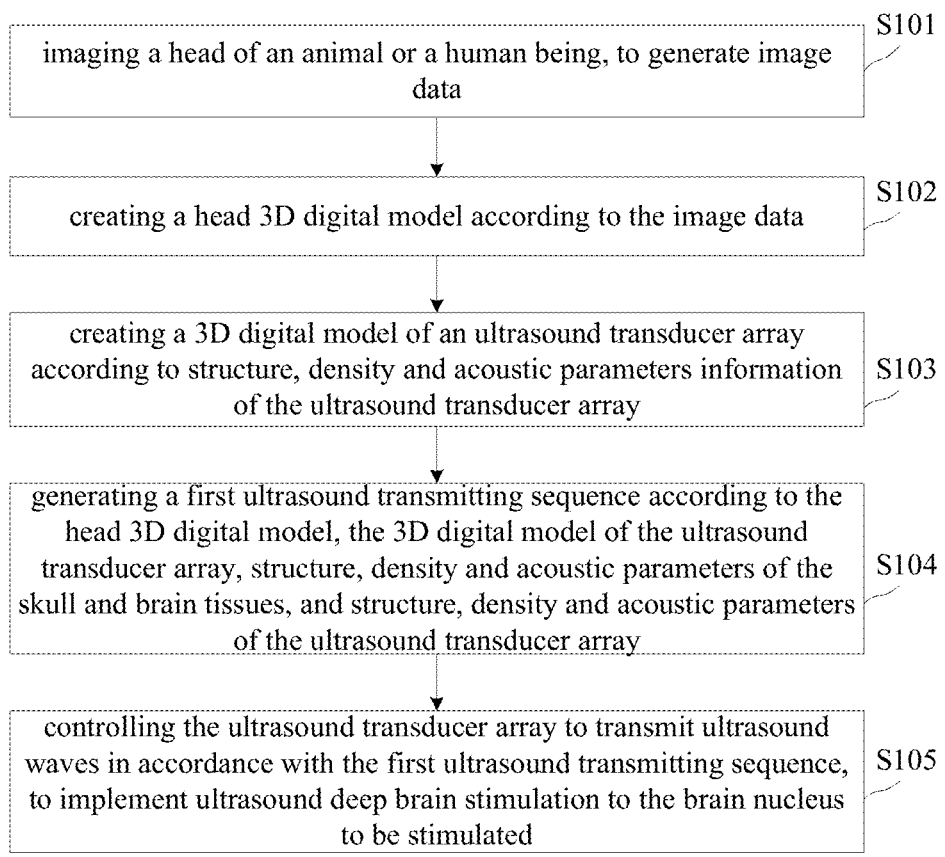
FIG. 1 is a flowchart of an ultrasound deep brain stimulation method according to an embodiment of the invention.

As shown in FIG. 1, the present invention provides an ultrasound deep brain stimulation method, comprising:

S101: medically imaging a head of an animal or a human being, to generate image data;

S102: creating a head 3D digital model according to the image data;

S103: creating a 3D digital model of an ultrasound transducer array according to structure, density and acoustic parameters information of the ultrasound transducer array;

S104: generating a first ultrasound transmitting sequence according to the head 3D digital model, the 3D digital model of the ultrasound transducer array, structure, density and acoustic parameters of the skull and brain tissues, and structure, density and acoustic parameters of the ultrasound transducer array;

S105: controlling the ultrasound transducer array to transmit ultrasound waves in accordance with the first ultrasound transmitting sequence, to implement ultrasound deep brain stimulation to the brain nucleus to be stimulated.

It can be seen from the flow as shown in FIG. 1 that, the present invention firstly creates a head 3D digital model and a 3D digital model of an ultrasound transducer array, obtains an ultrasound transmitting sequence according to the head 3D digital model and the 3D digital model of the ultrasound transducer array, and implements ultrasound deep brain stimulation to the brain nucleus to be stimulated by using the ultrasound transmitting sequence. Through the above flow, the invention can noninvasively pass through a skull to enter a deep brain region, to obtain an optimum ultrasound transmitting sequence required for transmitting transcranial focused ultrasound.

In specific implementation of the steps S101 and S102, a medical imaging equipment can be used to perform a head 3D magnetic resonance imaging scan and a 3D CT imaging scan on an animal or a human being that needs ultrasound deep brain stimulation, to obtain image data, and to perform 3D reconstruction and registration according to the obtained image data to create the head 3D digital model of the animal or the human being that includes structure, density and acoustic parameters of the skull and brain tissues, then import the head 3D digital model into a host control computer.

In another embodiment, besides the head 3D magnetic resonance imaging scan and the 3D CT imaging scan methods, a method in which any other medical imaging equipment that can image the head and the image is integrated into the head 3D digital model can be used as well, and the invention is not limited to this.

In one embodiment, the ultrasound deep brain stimulation method as shown in FIG. 1 further comprises: selecting position(s) of one or more brain nucleus to be stimulated, and locating the position of the brain nucleus to be stimulated at the head 3D digital model. This step may be performed after the step S102 and before the step S105, and the present invention does not specifically limit sequential relationship of this step with the steps S103 and S104.

Before the step S104, it is necessary to obtain structure and density of skull and brain tissues according to the head 3D digital model obtained in the step S102, and then to calculate acoustic parameters of the head according to the structure and density of the skull and brain tissues, the acoustic parameters including, but not limited to, sound velocity, and an attenuation coefficient.

Before specific implementation of the step S104, an ultrasound time reversal simulation software can be installed in the host control computer, then the 3D digital model of the ultrasound transducer array, the structure, density and acoustic parameters of the skull and brain tissues, the structure, density and acoustic parameters of the ultrasound transducer array, that are obtained in the steps S102 and S103, can be inputted to the ultrasound time reversal simulation software.

Figure 2:
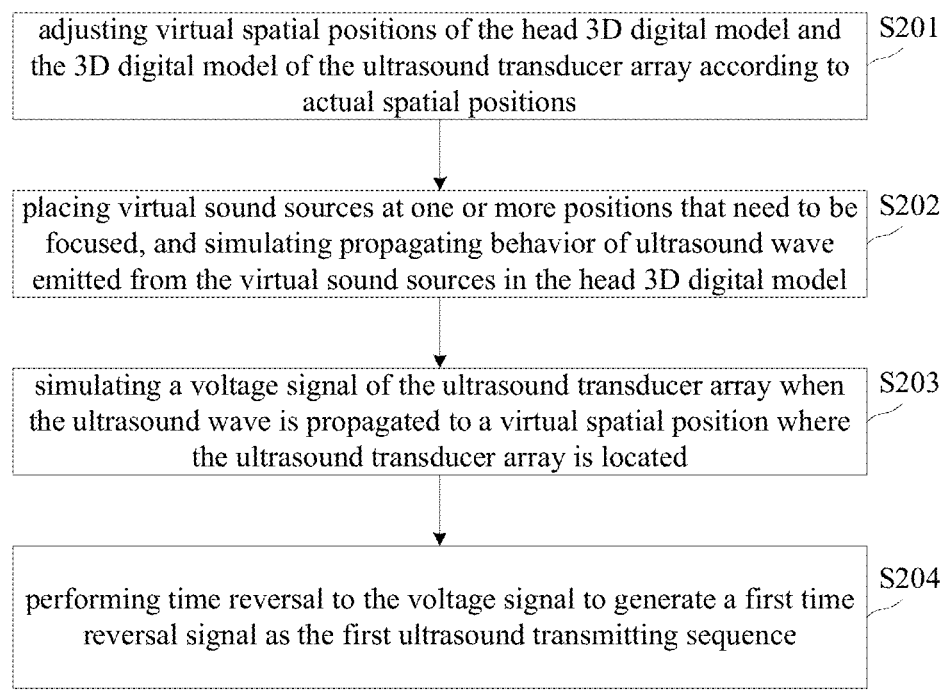
FIG. 2 is a flowchart of a method of generating an ultrasound transmitting sequence according to an embodiment of the invention.

As shown in FIG. 2, specific implementation of the step S104 includes the following steps:

S201: adjusting virtual spatial positions of the head 3D digital model and the 3D digital model of the ultrasound transducer array according to actual spatial positions, to adjust the virtual spatial positions of the head 3D digital model and the 3D digital model of the ultrasound transducer array at right positions in accordance with the actual spatial positions desired to be adopted.

S202: placing virtual sound sources at one or more positions that need to be focused, and simulating propagating behavior of ultrasound wave emitted from the virtual sound sources in the head 3D digital model.

S203: simulating a voltage signal of the ultrasound transducer array when the ultrasound wave is propagated to a virtual spatial position where the ultrasound transducer array is located. Specifically, when the ultrasound wave is propagated to a virtual spatial position where the ultrasound transducer array is located (the virtual spatial position that is adjusted at a right position in accordance with the actual spatial position desired to be adopted), simulating a sound intensity signal and a sound pressure signal of the ultrasound wave on ultrasound transducer array surface, and simulating a voltage signal of the ultrasound transducer array according to the sound intensity signal and the sound pressure signal and piezoelectric conversion parameters of the ultrasound transducer array, i.e., simulating a voltage signal of the ultrasound transducer after piezoelectric conversion from the sound intensity signal and the sound pressure signal.

S204: performing time reversal to the voltage signal to generate a first time reversal signal as the first ultrasound transmitting sequence.

Specifically, time reversal of the voltage signal is reversal in accordance with time sequence, and this method can be called a time reversal method. After the reversal in accordance with time sequence, the voltage signal is used for exciting the ultrasound transducer array to produce ultrasound wave which may be focused at one or more positions where virtual sound sources are placed in the step S202. Therefore, by the ultrasound time reversal simulation software, the present invention can obtain an ultrasound transmitting sequence that is required for stimulating the specified brain nucleus and can complete transcranial focus.

In specific implementation of the step S105, firstly a head of an animal or a human being that needs ultrasound deep brain stimulation is fixed at a specified position in a magnetic resonance imaging system by using a head fixing and locating device, and meanwhile the ultrasound transducer array is also fixed at a pre-designed position. The host control computer sends out an instruction to control the ultrasound transducer array by the ultrasound transmitting/receiving control system to perform ultrasound transmission in accordance with the ultrasound transmitting sequence.

The above-described modes for implementing ultrasound deep brain stimulation to the brain nucleus to be stimulated include: a pulse mode, a multiple period mode and an encoding mode, but the present invention is not limited to this.

Figure 3:
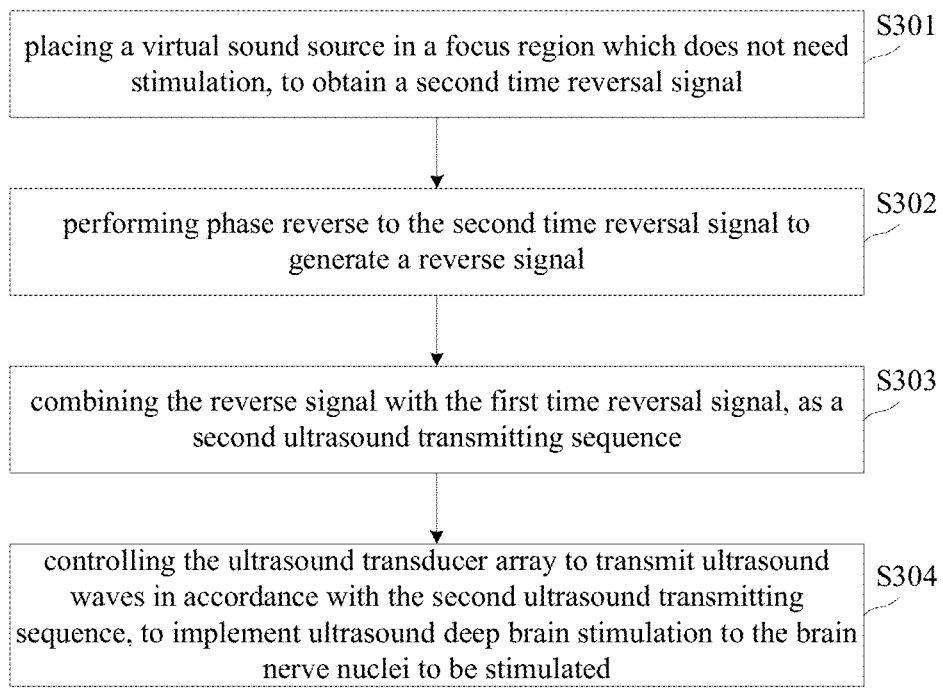
FIG. 3 is a flowchart of a processing method of removing a focused region according to an embodiment of the invention.

Furthermore, since acoustic field distribution of a certain intensity may be formed in an undesired focus region due to the above-described time reversal method, these focus regions that do not expect stimulation, as shown in FIG. 3, can be eliminated by the following method including:

S301: placing a virtual sound source in a focus region which does not need stimulation, to obtain a second time reversal signal;

S302: performing phase reverse to the second time reversal signal to generate a reverse signal;

S303: combining the reverse signal with the first time reversal signal, as a second ultrasound transmitting sequence;

S304: controlling the ultrasound transducer array to transmit ultrasound waves in accordance with the second ultrasound transmitting sequence, to implement ultrasound deep brain stimulation to the brain nucleus to be stimulated.

Through the method shown in FIG. 3, accuracy, effectiveness and safety of targeted neuromodulation can be further improved.

During ultrasound transmission in accordance with the first ultrasound transmitting sequence or the second ultrasound transmitting sequence, there is possibly position displacement and shape change of the focus point, in order to solve this problem, sound field focus position and shape after the ultrasound passes through the skull can be acquired by using an imaging sequence (a special imaging sequence) of a magnetic resonance imaging system, the first ultrasound transmitting sequence or the second ultrasound transmitting sequence can be adjusted according to the actually measured sound field focus position and shape in combination with the head 3D digital model, to change position and shape of an ultrasound focusing point to satisfy the requirement of ultrasound deep brain stimulation. The imaging sequence may be an imaging sequence in which tissue displacement produced by an ultrasonic sound field is observed, or an imaging sequence in which temperature change produced by the ultrasonic sound field is observed.

After the step S105, an ultrasound deep brain stimulation result (stimulation effect) can be acquired using a functional magnetic resonance imaging technology, the stimulation effect is observed and analyzed, and a fine tuning is performed to the ultrasound focusing position. Besides brain functional magnetic resonance imaging, the method of observing and evaluating the stimulation effect further includes, but not limited to, electroencephalogram, ultrasound brain function imaging and other methods.

The above-described ultrasound time reversal software is used for simulating an algorithm used in ultrasound propagation, which includes, but is not limited to, a linear wave equation, a nonlinear wave equation, a finite time difference method, a k space virtual spectrum method or the like. In specific implementation of the step S202, after the virtual sound sources are placed at one or more positions that need to be focused, the propagating behavior of ultrasound wave emitted from the virtual sound sources in the head 3D digital model can be simulated by using a linear wave equation, a nonlinear wave equation, a finite time difference method or a k space virtual spectrum method.

The ultrasound transducer array used in the ultrasound deep brain stimulation method according to the invention may be in various shapes, such as a flat plate, a sphere and an arc surface, and the like, and meanwhile the ultrasound transducer array is compatible with the magnetic resonance imaging system.

Figure 4:
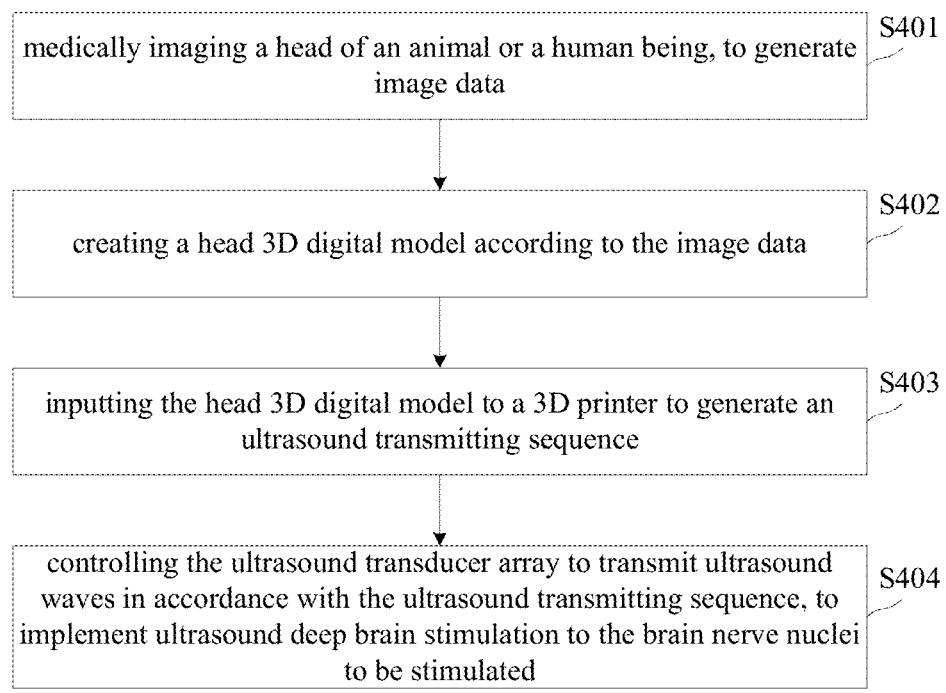
FIG. 4 is an ultrasound deep brain stimulation method according to another embodiment of the invention.

As shown in FIG. 4, an embodiment of the present invention provides an ultrasound deep brain stimulation method, comprising:

S401: medically imaging a head of an animal or a human being, to generate image data;

S402: creating a head 3D digital model according to the image data;

S403: inputting the head 3D digital model to a 3D printer to generate an ultrasound transmitting sequence;

S404: controlling the ultrasound transducer array to transmit ultrasound waves in accordance with the ultrasound transmitting sequence, to implement ultrasound deep brain stimulation to the brain nucleus to be stimulated.

It can be seen from the flow as shown in FIG. 4 that, the present invention firstly creates a head 3D digital model, inputs the head 3D digital model to a 3D printer to generate an ultrasound transmitting sequence, and implements ultrasound deep brain stimulation to the brain nucleus to be stimulated by using the ultrasound transmitting sequence. Through the above flow, the invention can obtain an optimum ultrasound transmitting sequence required for transmitting transcranial focused ultrasound.

In specific implementation of the steps S401 and S402, a medical imaging equipment can be used to perform a head 3D magnetic resonance imaging scan and a 3D CT imaging scan on an animal or a human being that needs ultrasound deep brain stimulation, to obtain image data, and to perform 3D reconstruction and registration of the obtained image data to create the head 3D digital model of the animal or the human being that includes structure, density and acoustic parameters of the skull and brain tissues, then import the head 3D digital model into a host control computer.

In another embodiment, besides the head 3D magnetic resonance imaging scan and the 3D CT imaging scan methods, a method in which any other medical imaging equipment that can image the head and the image is integrated into the head 3D digital model can be used as well, and the invention is not limited to this.

In one embodiment, the ultrasound deep brain stimulation method as shown in FIG. 4 further comprises: selecting position(s) of one or more brain nucleus to be stimulated, and locating the position of the brain nucleus to be stimulated at the head 3D digital model. This step may be performed after the step S402 and before the step S404, and the present invention does not specifically limit sequential relationship of this step with the step S403.

By using the head 3D digital model obtained in the step S402, the present invention can obtain structure and density of skull and brain tissues and then calculate acoustic parameters of the head according to the structure and density of the skull and brain tissues, the acoustic parameters including, but not limited to, sound velocity, and an attenuation coefficient.

Figure 5:
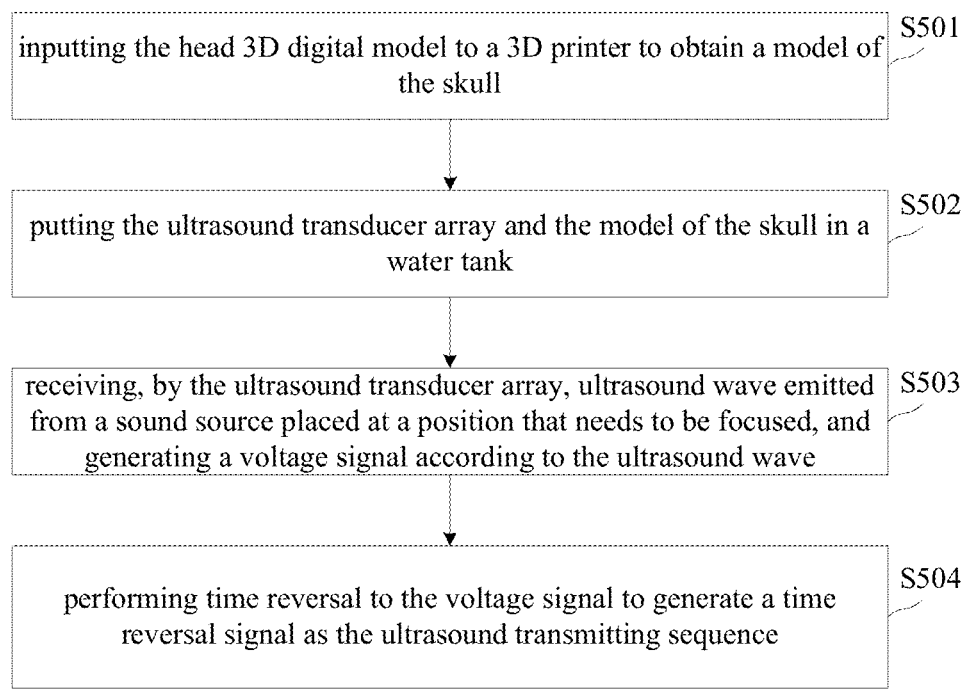
FIG. 5 is a flowchart of a method of generating an ultrasound transmitting sequence according to another embodiment of the invention.

As shown in FIG. 5, specific implementation of the step S403 includes the following steps:

S501: inputting the head 3D digital model to a 3D printer to obtain a model of the skull.

In specific implementation, it is necessary to input the head 3D digital model to the 3D printer, to duplicate the skull in accordance with the same size and structure using a 3D printing material having acoustic properties similar to that of the skull, to thereby obtain a skull model.

S502: putting the ultrasound transducer array and the model of the skull in a water tank.

S503: the ultrasound transducer array receives ultrasound wave emitted from a sound source placed at a position that needs to be focused, and generating a voltage signal according to the ultrasound wave.

In specific implementation of the step S503, the ultrasound transducer array or a hydrophone is placed as a sound source at a position that needs to be focused, the ultrasound wave sent out by the sound source is received by the ultrasound transducer array when it is propagated to the position where the ultrasound transducer array is located, and a series of voltage signals are obtained after piezoelectric conversion of the ultrasound wave.

S504: performing time reversal to the voltage signal to generate a time reversal signal as the ultrasound transmitting sequence.

In specific implementation of the step S504, the voltage signal is collected by the ultrasound transmitting/receiving control system, which converts the voltage signal into a digital signal and performs time reversal of the digital signal to be used for exciting the ultrasound transducer array to produce ultrasound wave that may be focused at the above-described position where the sound source is located. Therefore, as compared with the ultrasound deep brain stimulation method shown in FIG. 1, the present invention can also obtain an ultrasound transmitting sequence that is required for stimulating the specified brain nucleus and can complete transcranial focus, by the ultrasound deep brain stimulation method as shown in FIG. 4.

Time reversal of the above-described voltage signal is reversal in accordance with time sequence, and this method can be called a time reversal method.

In specific implementation of the step S404, firstly a head of an animal or a human being that needs ultrasound deep brain stimulation is fixed at a specified position in a magnetic resonance imaging system by using a head fixing and locating device, and meanwhile the ultrasound transducer array is also fixed at a pre-designed position. The host control computer sends out an instruction to control the ultrasound transducer array by the ultrasound transmitting/receiving control system to perform ultrasound transmission in accordance with the ultrasound transmitting sequence.

The above-described modes for implementing ultrasound deep brain stimulation to the brain nucleus to be stimulated include: a pulse mode, a multiple period mode and an encoding mode, but the present invention is not limited to this.

After the step S404, an ultrasound deep brain stimulation result (stimulation effect) can be acquired using a functional magnetic resonance imaging technology, the stimulation effect is observed and analyzed, and a fine tuning is performed to the ultrasound focusing position. Besides brain functional magnetic resonance imaging, the method of observing and evaluating the stimulation effect further includes, but not limited to, electroencephalogram, ultrasound brain function imaging and other methods.

During ultrasound transmission in accordance with the ultrasound transmitting sequence obtained in the step S404, there is possibly position displacement and shape change of the focus point, in order to solve this problem, sound field focus position and shape after the ultrasound passes through the skull can be acquired by using an imaging sequence (a special imaging sequence) of a magnetic resonance imaging system, the ultrasound transmitting sequence can be adjusted according to the actually measured sound field focus position and shape in combination with the head 3D digital model, to change position and shape of an ultrasound focusing point to satisfy the requirement of ultrasound deep brain stimulation. The imaging sequence may be an imaging sequence in which tissue displacement produced by an ultrasonic sound field is observed, or an imaging sequence in which temperature change produced by the ultrasonic sound field is observed.

The ultrasound transducer array used in the ultrasound deep brain stimulation method as shown in FIG. 4 may be in various shapes, such as a flat plate, a sphere and an arc surface, and the like, and meanwhile the ultrasound transducer array is compatible with the magnetic resonance imaging system.

Figure 6:
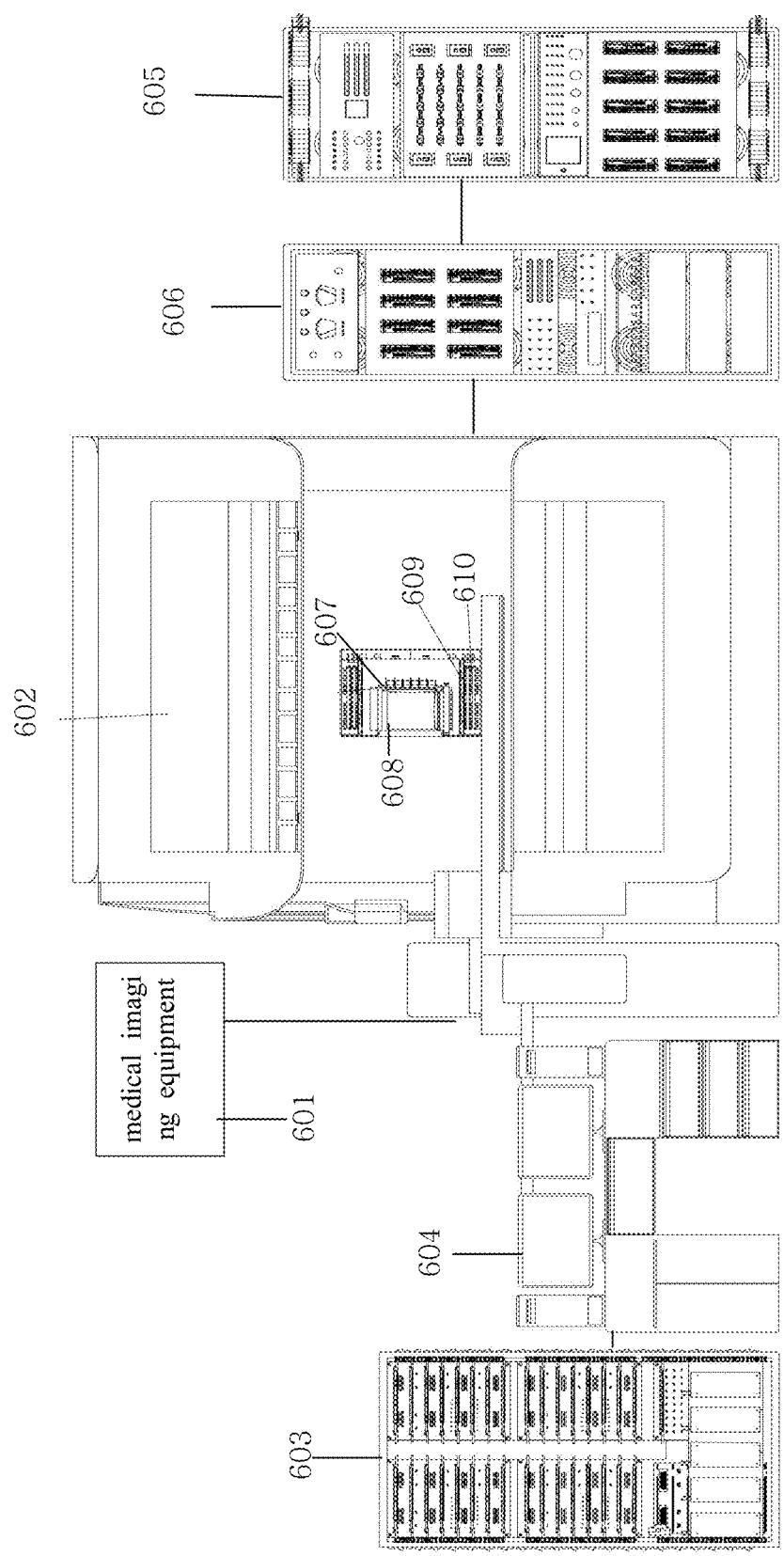
FIG. 6 is a structural schematic for illustrating an ultrasound deep brain stimulation system according to an embodiment of the invention.

As shown in FIG. 6, an embodiment of the present invention provides an ultrasound deep brain stimulation system, comprising: a medical imaging equipment 601, an MRI system 602, an ultrasound transmitting/receiving control system 603, a host control computer 604, an MRI control system 605 and a power supply management system 606.

The power supply management system 606 supplies power to the medical imaging equipment 601, the MRI system 602, the ultrasound transmitting/receiving control system 603, the host control computer 604 and the MRI control system 605.

The host control computer 604 is connected to the medical imaging equipment 601, the ultrasound transmitting/receiving control system 603 and the MRI control system 605, and the MRI system 602 is connected to the MRI control system 605.

The MRI system 602 is provided therein with an ultrasound transducer array 607 and a head fixing and locating device 608, wherein the head fixing and locating device 608 is used for fixing the head, the ultrasound transducer array 607 is disposed around the head fixing and locating device 608 and is connected to the ultrasound transmitting/receiving control system 603.

The medical imaging equipment 601 is used for photographing a head image of a human being or an animal, and reconstructing a head 3D digital model according to the head image of the human being or the animal Specifically, the medical imaging equipment 601 is used to perform a head 3D magnetic resonance imaging scan and a 3D CT imaging scan on an animal or a human being that needs ultrasound deep brain stimulation, to obtain image data, and to perform 3D reconstruction and registration of the obtained image data to create the head 3D digital model of the animal or the human being that includes structure, density and acoustic parameters of the skull and brain tissues, then import the head 3D digital model into the host control computer 604.

The host control computer 604 can obtain structure and density of skull and brain tissues according to the head 3D digital model, and then calculate acoustic parameters of the head according to the structure and density of the skull and brain tissues, the acoustic parameters including, but not limited to, sound velocity, and an attenuation coefficient.

The host control computer 604 may also create a 3D digital model of an ultrasound transducer array according to structure, shape and acoustic parameters information of the ultrasound transducer array.

An ultrasound time reversal simulation software is installed in the host control computer 604, and the 3D digital model of the ultrasound transducer array, the structure, density and acoustic parameters of the skull and brain tissues, the structure, density and acoustic parameters of the ultrasound transducer array are inputted to the ultrasound time reversal simulation software, to obtain the ultrasound transmitting sequence specifically as follows:

adjusting virtual spatial positions of the head 3D digital model and the 3D digital model of the ultrasound transducer array according to actual spatial positions; placing virtual sound sources at one or more positions that need to be focused, and simulating propagating behavior of ultrasound wave emitted from the virtual sound sources in the head 3D digital model; when the ultrasound wave is propagated to a virtual spatial position where the ultrasound transducer array is located, simulating a sound intensity signal and a sound pressure signal of the ultrasound wave on ultrasound transducer array surface, and simulating a voltage signal of the ultrasound transducer array according to the sound intensity signal and the sound pressure signal and piezoelectric conversion parameters of the ultrasound transducer array. Time reversal is performed to the voltage signal to generate a first time reversal signal as the ultrasound transmitting sequence. After the reversal in accordance with time sequence, the voltage signal is used for exciting the ultrasound transducer array to produce ultrasound wave which may be focused at one or more positions where virtual sound sources are placed.

After obtaining the ultrasound transmitting sequence, the host control computer 604 sends out an ultrasound deep brain stimulation instruction to the ultrasound transmitting/receiving control system 603.

The ultrasound transmitting/receiving control system 603 receives the ultrasound deep brain stimulation instruction, controls the ultrasound transducer array according to the ultrasound deep brain stimulation instruction to transmit ultrasound wave to the brain nucleus to be stimulated in accordance with the ultrasound transmitting sequence to implement ultrasound deep brain stimulation.

The MRI control system 605 controls the MRI system 602 to monitor actual position and shape of an ultrasound focusing point in real time, and can adjust the ultrasound transmitting sequence according to frequency, pulse duration, pulse length, pulse repetition frequency and intensity.

In one embodiment, the ultrasound deep brain stimulation system as shown in FIG. 6 further comprises: a 3D printer, a water tank and a sound source, not shown in the figure. The 3D printer is used for printing a skull model according to the head 3D digital model, the water tank is used for housing the skull model and the ultrasound transducer array, the sound source is placed at the position to be focused and is used for sending out ultrasound wave to the ultrasound transducer array placed in the water tank.

The MRI system 602 uses an RF coil 609 and a gradient coil 610. As for an RF subsystem (an RF coil), a fast parallel imaging technology based on multi-channel RF transmitting and receiving is needed. As for a gradient subsystem (a gradient coil), as compared with a clinical system which needs an obviously improved gradient intensity and gradient rise rate, the gradient subsystem also has good stability and low noise.

In one embodiment, the shape of the ultrasound transducer array includes: a flat plate, a sphere and an arc surface and etc., but the present invention is not limited to this.

The ultrasound deep brain stimulation methods as shown in FIGS. 1 and 4 can both be used in the ultrasound deep brain stimulation system, wherein the ultrasound deep brain stimulation method as shown in FIG. 1 does not need a 3D printer and a water tank, while the ultrasound deep brain stimulation method as shown in FIG. 4 needs a 3D printer and a water tank.

The present invention provides a new, safe, effective and noninvasive ultrasound deep brain stimulation method and system, which can realize fixed-point specificity neural network regulation, multi-point network neuromodulation and research on physical mechanisms for neuromodulation, is helpful to develop potential therapy of central nervous system diseases, and also provides powerful new means for exploring normal human brain functions, understanding cognition, decision making and thinking, and accurately knowing about activities of neural circuits. Therefore, the ultrasound deep brain stimulation method and system are expected to become important scientific instruments for neurosciences and brain disease research.

The ultrasound deep brain stimulation system of the present invention is compatible with an MRI imaging system, monitors ultrasound neuromodulation information (focus, structural function, Bold signal and etc.) using the fMRI in real time, and meanwhile realizes fixed-point specificity neural network regulation, multi-point network neuromodulation, and further realizes a regulating effect of the ultrasound neuromodulation on the neural circuits and research on a regulating mechanism (an acoustic radiation force, acoustic streaming, shock wave, cavitation effect and etc.).

The ultrasound deep brain stimulation method and system of the present invention can realize research on a physical mechanism for ultrasound neuromodulation: realizing different neuromodulation functions by adjusting ultrasound parameters (frequency, PRF, intensity, pulse duration and etc.) (realizing different degrees of stimulation or suppressing nerve excitability, realizing the expected different physical or emotional responses by neuromodulation, and producing targeted therapy effects on different neurological diseases, and etc.).

The ultrasound deep brain stimulation method and system of the present invention can realize personalized specificity neuromodulation: even the same neurological disease may behave differently on different patients, so that a single neuromodulation measure is not adaptable to all cases. The present invention integrates medical image information such as magnetic resonance, CT and the like, establishes a personalized head 3D digital model to guide neuromodulation process (locating and navigation and etc.), and observes, evaluates and regulates the regulation effect using various functional medical imaging methods, thereby can realize personalized specificity neuromodulation of the patients.

The ultrasound deep brain stimulation method and system of the present invention can realize multi-point circuit horizontal regulation: the method that is used for obtaining an ultrasound transmitting sequence for realizing transcranial focus by using ultrasound time reversal principle, can inventively realize simultaneous or successive stimulation to multiple key nodes on the neural circuit, or realize simultaneous or successive stimulation on a continuous region of the whole neural circuit.

The ultrasound deep brain stimulation method and system of the present invention can realize accurate control of neuromodulation stimulation scope: since there may still be sound field distribution of a certain intensity formed by the time reversal method in regions that are not desired to be focused, in these regions that are not desired to be focused, it is practicable, by the above method, to firstly place virtual sound sources to obtain time reversal signals, and then transmit time reversal ultrasound signals at negative phase to eliminate sound field intensity of the regions, so that accuracy, effectiveness and safety of targeted neuromodulation can be further improved.

The ultrasound deep brain stimulation system of the present invention can achieve to possess a number of hardwares that are far more than the number of common ultrasound imaging equipments, can realize transmission and reception of ultrasound signals of ten thousand channels, each of which is controlled independently, and any waveform is used in a breakthrough manner for exciting transmission of the ultrasound signals to complete time reversal of the ultrasound signals.

Based on the ultrasound focus positioning technology characteristics of magnetic resonance imaging, using one-dimensional imaging technology, the present invention can avoid interference to displacement monitoring caused by macroscopic motion; motion sensitizing gradient needs to be synchronized with the ultrasound effect and can be added in any spatial direction; accuracy of a displacement diagram is in direct proportion to an image signal to noise ratio.

By adopting magnetic resonance imaging guidance and noninvasive temperature measurement technologies, the present invention decides accuracy of ultrasound deep brain stimulation and regulation effects. As for an RF subsystem (an RF coil), the present invention adopts a fast parallel imaging technology based on multi-channel RF transmitting and receiving. As for a gradient subsystem (a gradient coil), as compared with a clinical system which needs an obviously improved gradient intensity and gradient rise rate, the gradient subsystem also has good stability and low noise.

In conclusion, the ultrasound deep brain stimulation system and method of the present invention can provide a high spatial resolution (1~2 mm), and can noninvasively passes through the skull to enter a deep brain region. An optimum ultrasound transmitting sequence required for transmitting transcranial focused ultrasound by an ultrasound time reversal method, and actual position and shape of the ultrasound focusing point can be monitored in real time by the magnetic resonance imaging system, to adjust the transmitting sequence depending on time (frequency, pulse duration, pulse length, pulse repetition frequency, intensity, and etc.), so as to realize targeted region regulation.

Figure 7A:
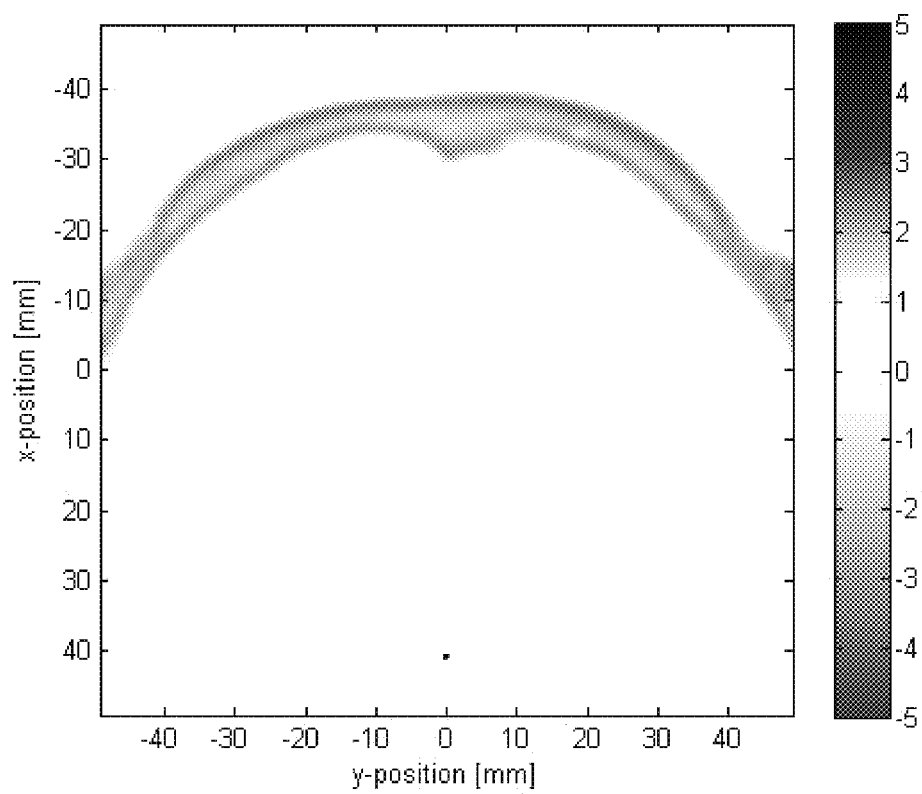
FIGS. 7A and 7B are schematics of simulation experiment results of a method of generating an ultrasound transmitting sequence required for realizing transcranial focus according to an embodiment of the invention.
Figure 7B:
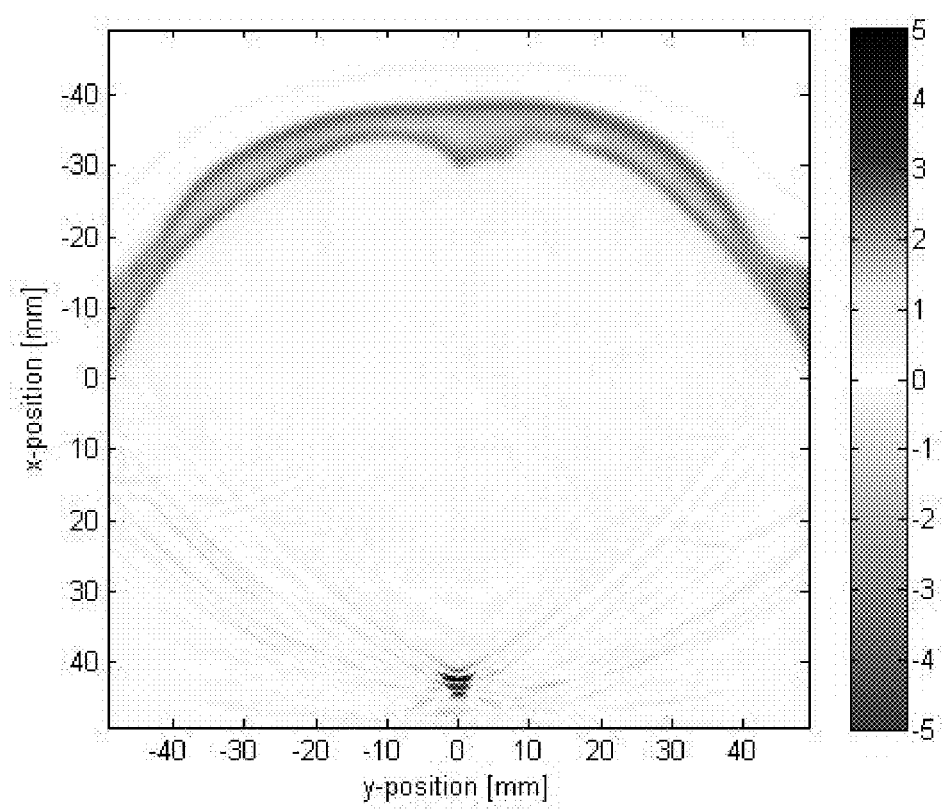

By using an ultrasound time reversal software in a two-dimensional plane, the present invention obtains a simulation experiment which realizes the method of generating an ultrasound transmitting sequence required for transcranial focus. Experiment results are as shown in FIGS. 7A and 7B, in which a dot at (0, 40) in FIG. 7A is an initial position of a virtual sound source, and FIG. 7B shows ultrasound focus effect that is realized by simulation through the time reversal method; top border of the figure is a linear array ultrasound transducer array. Grey portions in FIGS. 7A and 7B are skull models reconstructed from a CT scan image, in which acoustic parameters of the head are calculated according to structure and density of skull and brain tissues, and the acoustic parameter are imported into the simulation software to be set as corresponding numerical values corresponding to calculation nodes on the two-dimensional plane. It can be seen from the simulation results that, although horizontal and vertical sizes of ultrasound focus points after time reversal transmission are increased as compared with the size of the original sound source, most of the energy is still concentrated at the preset position, which can satisfy requirements of accurate fixed-point stimulation and that other regions around are affected to a small extent. The demand of the present invention can be satisfied as long as the method is extended from a two-dimensional plane to a 3D spatial digital model.

In the experiment of ultrasound stimulation of a mouse brain to induce an action response, after the mouse is narcotized, hair on the top of the head is removed, and then the head is fixed on a brain solid positioner. The ultrasound transducer array is accurately positioned by the brain solid positioner, and is attached close to the skull to radiate pulsed ultrasound to the motor cortex. The ultrasound stimulation can synchronously induce the mouse to make a body movement response.

Persons skilled in the art shall understand that, the embodiments of the present invention can be provided as a method, a system or a computer program product. Therefore, the present invention can adopt the forms of a full hardware example, a full software example, or combination of a software example and a hardware example. Moreover, the present invention can adopt the form of a computer program product that is implemented on one or more computer-usable storage medium (including but not limited to a disk memory, a CD-ROM, an optical memory, and etc.) including computer-usable program codes.

The invention is described with reference to flow diagrams and/or block diagrams of the method, the device (system) and the computer program product according to the embodiment of the invention. It should be understood that each flow and/or block in the flow diagrams and/or block diagrams, and the combination of the flows and/or blocks in the flow diagrams and/or block diagrams can be achieved by computer program commands. These computer program commands can be provided to a CPU of a general-purpose computer, a special-purpose computer, an embedded processor or other programmable data processing device to produce a machine, so that a device for achieving functions designated in one or more flows in the flow diagrams and/or one or more blocks in the block diagrams can be generated by the command executed by the CPU of the computer or other programmable data processing device.

These computer program commands can also be stored in a computer-readable memory that can guide a computer or other programmable data processing device to operate in a special way, so that the command stored in the computer-readable memory generates a manufactured product including a command device which achieves functions designated in one or more flows in the flow diagrams and/or one or more blocks in the block diagrams.

These computer program commands can also be loaded on a computer or other programmable data processing device, on which a series of operation steps are executed to generate processing achieved by the computer, so that the command executed on the computer or other programmable data processing device is provided for being used in the steps of achieving functions designated in one or more flows in the flow diagrams and/or one or more blocks in the block diagrams.

The invention adopts specific embodiments to explain the principle and implementation way of the invention. The above embodiments are described merely for helping to understand the method and core concept of the invention; in addition, a person skilled in the art can, on the basis of the concept of the invention, make modifications to both of the specific embodiments and application scope. In conclusion, contents disclosed herein should not be understood as limitation to the invention.

The invention claimed is:

1. An ultrasound deep brain stimulation method, comprising:
   medically imaging a head of an animal, to generate image data;
   creating a head 3D digital model according to the image data;
   using a medical imaging equipment to perform a head 3D magnetic resonance imaging scan and a 3D CT imaging scan on an animal that needs ultrasound deep brain stimulation, to obtain image data, and to perform 3D reconstruction and registration according to the obtained image data to create the head 3D digital model of the animal that includes structure, density and acoustic parameters of the skull and brain tissues, then importing the head 3D digital model into a host control computer;
   creating a 3D digital model of an ultrasound transducer array according to structure, density and acoustic parameters information of the ultrasound transducer array;
   generating a first ultrasound transmitting sequence according to the head 3D digital model, the 3D digital model of the ultrasound transducer array, structure, density and acoustic parameters of the skull and brain tissues, and structure, density and acoustic parameters of the ultrasound transducer array, the generating step comprises:

adjusting virtual spatial positions of the head 3D digital model and the 3D digital model of the ultrasound transducer array according to actual spatial positions, to adjust the virtual spatial positions of the head 3D digital model and the 3D digital model of the ultrasound transducer array at right positions in accordance with the actual spatial positions desired to be adopted;

placing virtual sound sources at one or more positions that need to be focused on, and simulating propagating behavior of ultrasound wave emitted from the virtual sound sources in the head 3D digital model;

simulating a voltage signal of the ultrasound transducer array when the ultrasound wave is propagated to a virtual spatial position where the ultrasound transducer array is located;

when the ultrasound wave is propagated to a virtual spatial position where the ultrasound transducer array is located, simulating a sound intensity signal and a sound pressure signal of the ultrasound wave on ultrasound transducer array surface, and simulating a voltage signal of the ultrasound transducer array according to the sound intensity signal and the sound pressure signal and piezoelectric conversion parameters of the ultrasound transducer array;

performing time reversal to the voltage signal to generate a first time reversal signal as the first ultrasound transmitting sequence;

time reversal of the voltage signal being reversal in accordance with time sequence, after the reversal in accordance with time sequence, the voltage signal being used for exciting the ultrasound transducer array to produce ultrasound wave which may be focused on at one or more positions where virtual sound sources are placed;

controlling the ultrasound transducer array to transmit ultrasound waves in accordance with the first ultrasound transmitting sequence, to implement ultrasound deep brain stimulation to the brain nucleus to be stimulated;

fixing a head of an animal that needs ultrasound deep brain stimulation at a specified position in a magnetic resonance imaging system by using a head fixing and locating device, and fixing the ultrasound transducer array at a pre-designed position; after fixing the head of the animal and fixing the ultrasound transducer array, the host control computer sending out an instruction to control the ultrasound transducer array by an ultrasound transmitting/receiving control system to perform ultrasound transmission in accordance with the first ultrasound transmitting sequence.

2. The ultrasound deep brain stimulation method according to claim 1, wherein, the ultrasound deep brain stimulation method further comprises: selecting position(s) of one or more brain nucleus to be stimulated, and locating the position of the brain nucleus to be stimulated at the head 3D digital model.

3. The ultrasound deep brain stimulation method according to claim 2, wherein, simulating a voltage signal of the ultrasound transducer array when the ultrasound wave is propagated to a virtual spatial position where the ultrasound transducer array is located comprises:

simulating a sound intensity signal and a sound pressure signal of the ultrasound wave on ultrasound transducer array surface, and simulating a voltage signal of the ultrasound transducer array according to the sound intensity signal and the sound pressure signal and piezoelectric conversion parameters of the ultrasound transducer array.

4. The ultrasound deep brain stimulation method according to claim 3, wherein, the ultrasound deep brain stimulation method further comprises: adjusting virtual transducer positions on the head 3D digital model to correspond to real transducer positions on the head or a 3D physical model of the head.

5. The ultrasound deep brain stimulation method according to claim 4, characterized in that, the ultrasound deep brain stimulation method further comprises: calculating acoustic parameters of the head according to the structure and density of the skull and brain tissues.

6. The ultrasound deep brain stimulation method according to claim 5, wherein, the ultrasound deep brain stimulation method further comprises:

placing the virtual sound source in a focus region which does not need stimulation and obtaining a second time reversal signal;

performing phase reverse to the second time reversal signal to generate a reverse signal;

combining the reverse signal with the first time reversal signal, as a second ultrasound transmitting sequence;

controlling the ultrasound transducer array to transmit ultrasound waves in accordance with the second ultrasound transmitting sequence, to implement ultrasound deep brain stimulation to the brain nucleus to be stimulated.

7. The ultrasound deep brain stimulation method according to claim 6, wherein, the ultrasound deep brain stimulation method further comprises: acquiring sound field focus position and shape after the ultrasound passes through the skull by using an imaging sequence of a magnetic resonance imaging system, and adjusting the first ultrasound transmitting sequence or the second ultrasound transmitting sequence according to the sound field focus position and shape and the head 3D digital model to change position and shape of an ultrasound focusing point.

8. The ultrasound deep brain stimulation method according to claim 7, wherein, an ultrasound deep brain stimulation result is acquired using a functional magnetic resonance imaging technology, and a fine tuning is performed to an ultrasound focusing position according to the ultrasound deep brain stimulation result.

9. The ultrasound deep brain stimulation method according to claim 1, wherein, the medically imaging a head of an animal, to generate image data comprises: performing a 3D magnetic resonance imaging scan and a 3D CT imaging scan to the head of an animal, to generate image data.

10. The ultrasound deep brain stimulation method according to claim 9, wherein, creating a head 3D digital model according to the image data comprises: performing 3D reconstruction and registration of the image data, to create the head 3D digital model of the animal that includes structure, density and acoustic parameters of the skull and brain tissues.

11. The ultrasound deep brain stimulation method according to claim 3, wherein, placing virtual sound sources at one or more positions that need to be focused on, and simulating propagating behavior of ultrasound wave emitted from the virtual sound sources in the head 3D digital model comprises: simulating propagating behavior of ultrasound wave emitted from the virtual sound sources in the head 3D digital model by using a linear wave equation, a nonlinear wave equation, a finite time difference method or a k space virtual spectrum method.

12. The ultrasound deep brain stimulation method according to claim 1, wherein, the shape of the ultrasound transducer array being a flat plate, a sphere or an arc surface, and meanwhile the ultrasound transducer array is compatible with the magnetic resonance imaging system.

13. The ultrasound deep brain stimulation method according to claim 7, wherein, the imaging sequence is an imaging sequence in which tissue displacement produced by an ultrasonic sound field is observed, or an imaging sequence in which temperature change produced by the ultrasonic sound field is observed.

14. The ultrasound deep brain stimulation method according to claim 1, wherein, modes for implementing ultrasound deep brain stimulation to the brain nucleus to be stimulated include: a pulse mode, a multiple period mode and an encoding mode.

15. An ultrasound deep brain stimulation system, comprising: a medical imaging equipment, an MRI system, an ultrasound transmitting/receiving control system, a host control computer, an MRI control system and a power management system; the host control computer is connected to the medical imaging equipment, the ultrasound transmitting/receiving control system and the MRI control system; the MRI system is connected to the MRI control system; the MRI system is provided therein with an ultrasound transducer array, a head fixing and locating device, wherein the head fixing and locating device is used for fixing the head, the ultrasound transducer array is disposed around the head fixing and locating device and is connected to the ultrasound transmitting/receiving control system; the medical imaging equipment being used to perform a head 3D magnetic resonance imaging scan and a 3D CT imaging scan on an animal that needs ultrasound deep brain stimulation, to obtain image data, and to perform 3D reconstruction and registration according to the obtained image data to create a head 3D digital model of the animal that includes structure, density and acoustic parameters of the skull and brain tissues, then importing the head 3D digital model into a host control computer;

the medical imaging equipment, comprising: a first processor for photographing a head image, and reconstructing a head 3D digital model according to the head image;

the host control computer, comprising: a second processor for creating a 3D digital model of the ultrasound transducer array according to structure, density and acoustic parameter information of the ultrasound transducer array, and generating an ultrasound transmitting sequence according to the head 3D digital model and the 3D digital model of the ultrasound transducer array, and then sending an ultrasound deep brain stimulation instruction to the ultrasound transmitting/receiving control system; specifically, generating the ultrasound transmitting sequence according to the head 3D digital model and the 3D digital model of the ultrasound transducer array, and then sending the ultrasound deep brain stimulation instruction to the ultrasound transmitting/receiving control system, comprises:

adjusting virtual spatial positions of the head 3D digital model and the 3D digital model of the ultrasound transducer array according to actual spatial positions, to adjust the virtual spatial positions of the head 3D digital model and the 3D digital model of the ultrasound transducer array at right positions in accordance with the actual spatial positions desired to be adopted;

placing virtual sound sources at one or more positions that need to be focused on, and simulating propagating behavior of ultrasound wave emitted from the virtual sound sources in the head 3D digital model;

simulating a voltage signal of the ultrasound transducer array when the ultrasound wave is propagated to a virtual spatial position where the ultrasound transducer array is located;

when the ultrasound wave is propagated to a virtual spatial position where the ultrasound transducer array is located, simulating a sound intensity signal and a sound pressure signal of the ultrasound wave on ultrasound transducer array surface, and simulating a voltage signal of the ultrasound transducer array according to the sound intensity signal and the sound pressure signal and piezoelectric conversion parameters of the ultrasound transducer array;

performing time reversal to the voltage signal to generate a first time reversal signal as the ultrasound transmitting sequence;

time reversal of the voltage signal being reversal in accordance with time sequence, after the reversal in accordance with time sequence, the voltage signal being used for exciting the ultrasound transducer array to produce ultrasound wave which may be focused on at one or more positions where virtual sound sources are placed;

the ultrasound transmitting/receiving control system, comprising: a receiver for receiving the ultrasound deep brain stimulation instruction, controlling the ultrasound transducer array according to the ultrasound deep brain stimulation instruction to transmit ultrasound wave to the brain nucleus to be stimulated in accordance with the ultrasound transmitting sequence to implement ultrasound deep brain stimulation;

the MRI control system controls the MRI system, comprising: a third processor for monitoring actual position and shape of an ultrasound focusing point in real time, adjusting the ultrasound transmitting sequence according to frequency, pulse duration, pulse length, pulse repetition frequency and intensity.

16. The ultrasound deep brain stimulation system according to claim 15, wherein, the ultrasound deep brain stimulation system further comprises: a 3D printer, a water tank and a sound source;

the 3D printer is used for printing a skull model according to the head 3D digital model;

the water tank is used for housing the skull model and the ultrasound transducer array;

the sound source is placed at a position to be focused on, for sending out ultrasound wave to the ultrasound transducer array placed in the water tank.

17. The ultrasound deep brain stimulation system according to claim 16, wherein, the shape of the ultrasound transducer array being a flat plate, a sphere or an arc surface, and meanwhile the ultrasound transducer array is compatible with the magnetic resonance imaging system.

* * * * *